US005779705A

United States Patent [19]

Matthews

[11] Patent Number: 5,779,705

[45] Date of Patent: Jul. 14, 1998

[54] INTRAMEDULLARY NAIL

[76] Inventor: Michael Gordon Matthews, Orchard Farm, Little Kingshill, Great Missenden Buckinghamshire HP16 OEB, Great Britain

[21] Appl. No.: 750,165

[22] PCT Filed: Jun. 9, 1995

[86] PCT No.: PCT/GB95/01355

§ 371 Date: Dec. 18, 1996

§ 102(e) Date: Dec. 18, 1996

[87] PCT Pub. No.: WO95/34248

PCT Pub. Date: Dec. 12, 1995

[30] Foreign Application Priority Data

Jun. 10, 1994 [GB] United Kingdom .................. 9411693

[51] Int. Cl.[6] .................................................. A61B 17/56

[52] U.S. Cl. ................................ 606/67; 606/62; 606/64; 606/96

[58] Field of Search ................................ 606/62, 63, 64, 606/65, 66, 67, 88, 98, 96, 97

[56] References Cited

U.S. PATENT DOCUMENTS 4,473,069 9/1984 Kolmert .
4,622,959 11/1986 Marcus .
4,911,153 3/1990 Border .................................... 606/98
5,443,466 8/1995 Shah ........................................ 606/62
5,549,610 8/1996 Russell et al. ........................... 606/64
5,609,595 3/1997 Pennig .................................... 606/65

FOREIGN PATENT DOCUMENTS 0 355 411 A1 2/1990 European Pat. Off. .
2 636 226 11/1990 France .
4240277 6/1993 Germany ................................ 606/96
2 274 993 8/1994 United Kingdom .

*Primary Examiner*—Michael Buiz
*Assistant Examiner*—Julian W. Woo
*Attorney, Agent, or Firm*—Burns, Doane Swecker & Mathis LLP

[57] ABSTRACT

This invention relates to a surgical intramedullary nail, for stabilization of condylar and supracondylar fractures of the femur. It incorporates a Cruciate arrangement of two obliquely crossing locking bolts such that each condyle of the femur is gripped by an individual bolt. By this means both femoral condyles are stabilized with respect to the shaft of the femur. The bolts are oriented so that each passes through the main extra-articular mass of each condyle. Further predrilled holes are provided for insertion of proximal locking bolts to stabilize the nail with respect to the shaft of the femur. The nail is intended for retrograde insertion from distal to proximal into the intramedullary canal of the femur. Insertion of the locking bolts may be facilitated by the use of a temporary jig which is attached securely to the distal end of the nail. Nails of similar design can be used for stabilization of equivalent fractures of the humerus.

10 Claims, 5 Drawing Sheets

35
10
30
25
26
262
20
261
21
212
211
11

View on XX

Linear dimensions in mm
Angular dimensions in degrees

View on AA

View on BB

INTRAMEDULLARY NAIL

BACKGROUND OF THE INVENTION

1. Field of the Invention

This invention relates to surgical intramedullary nails for stabilizing condylar and supracondylar fractures, particularly of the distal femur or humerus.

2. Description of Related Art

The use of inert metal rods or tubes inserted into the intramedullary cavity of long bones in order to stabilise fractures is well established in orthopaedic and veterinary practice. These rods or tubes are usually referred to as "nails".

Fractures in the middle third of a long bone may be effectively stabilized with a simple intramedullary nail.

The effectiveness of this method may be increased by the use of cross bolts or screws passing through pre-drilled holes in the nail, so as to achieve better hold on the proximal and distal bone fragments.

Nails with cross bolts have become known as "locking" or "locked" nails. These nails have broadened the use of the method to fractures extending well into the proximal or distal ends.

The insertion of the cross bolts/screws may be facilitated by the use of a guide jig which attaches temporarily to the end of the intramedullary nail, but this is not invariable and many systems require at least some of the cross bolts/screws to be inserted freehand.

In cases where the fracture is in the vicinity of the condylar region of the femur or humerus, difficulties may be encountered in stabilizing the distal condylar fragments in relation to the shaft of the bone.

SUMMARY

The present invention comprises an intramedullary surgical nail designed for retrograde or reversed insertion into the distal end of the femur or humerus. It incorporates a unique staggered/crossed or "Cruciate" configuration of holes, so that two distal locking bolts may be inserted. This arrangement permits the locking bolts to cross and overlap so that each condyle may be ripped by an individual bolt. Both condyles are thereby stabilized in relation to the shaft of the bone, along which the intramedullary nail passes.

The nails may also incorporate further pre-formed holes at their proximal ends so that further cross bolts may be inserted to improve the fixation of the nail with respect to the more proximal femoral or humeral shaft. Such further holes are usually arranged so that when cross bolts are inserted, they extend at right angles to the nail.

BRIEF DESCRIPTION OF THE DRAWINGS

Features of the femoral and humeral nails in accordance with the invention and a jig for introducing the nails and locking bolts are illustrated in the accompanying drawings:

DETAILED DESCRIPTION OF THE PREFERRED EMBODIMENTS

Figure 1:
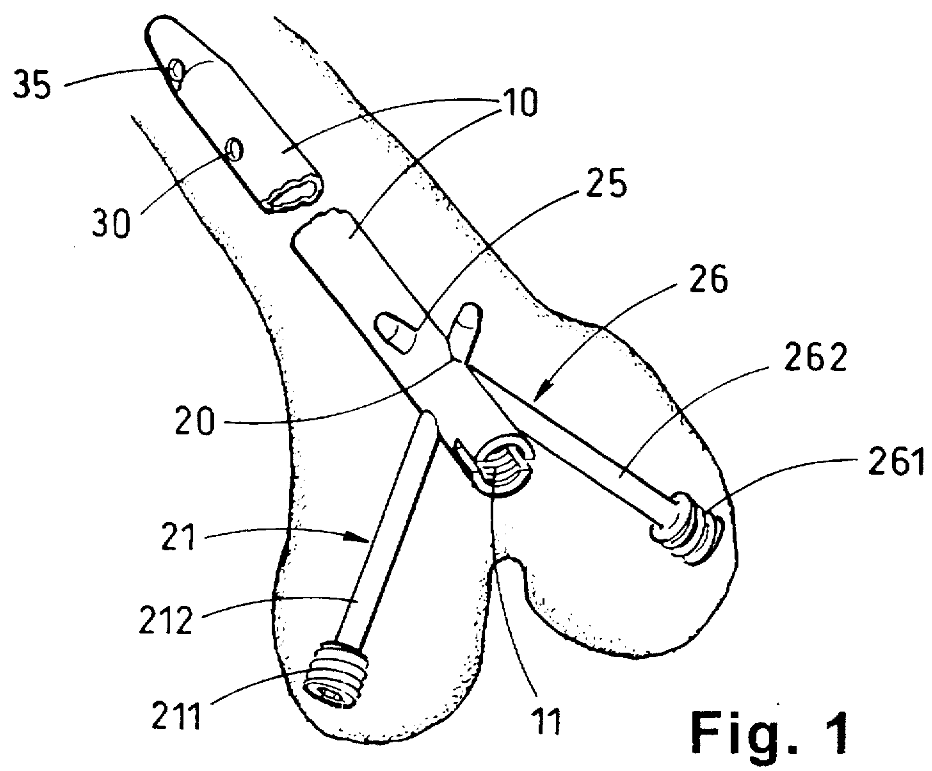
Figure 2:
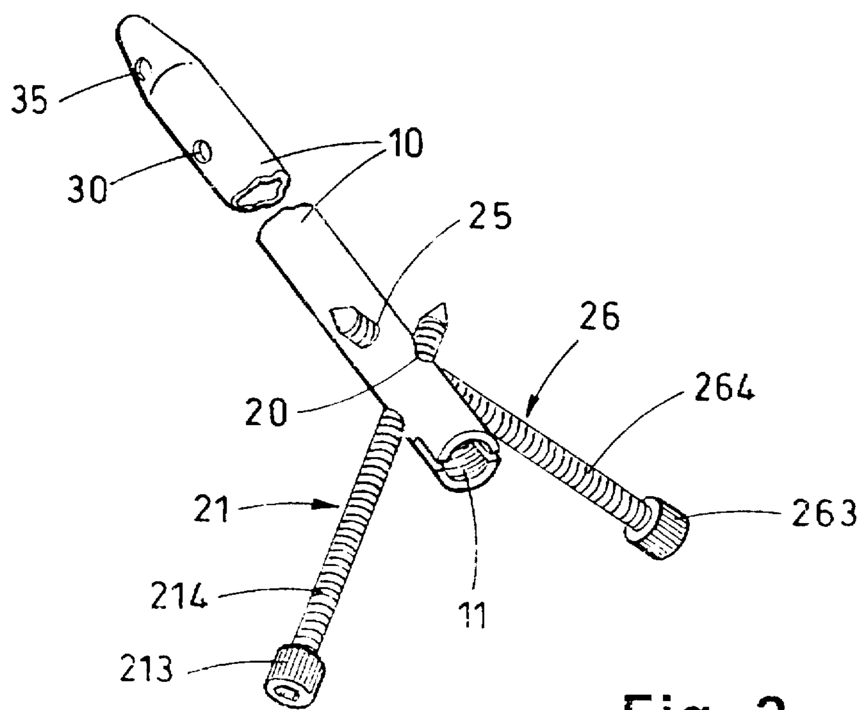
Figure 3:
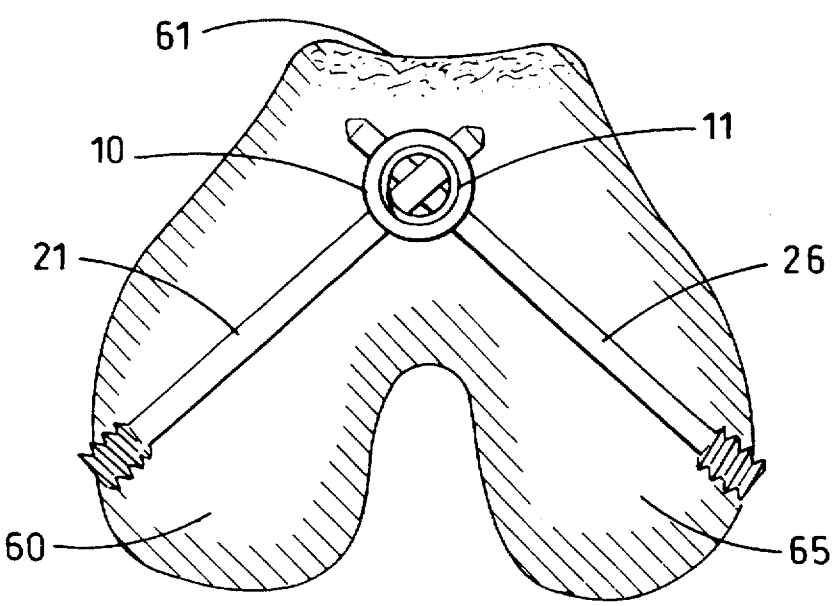
Figure 4:
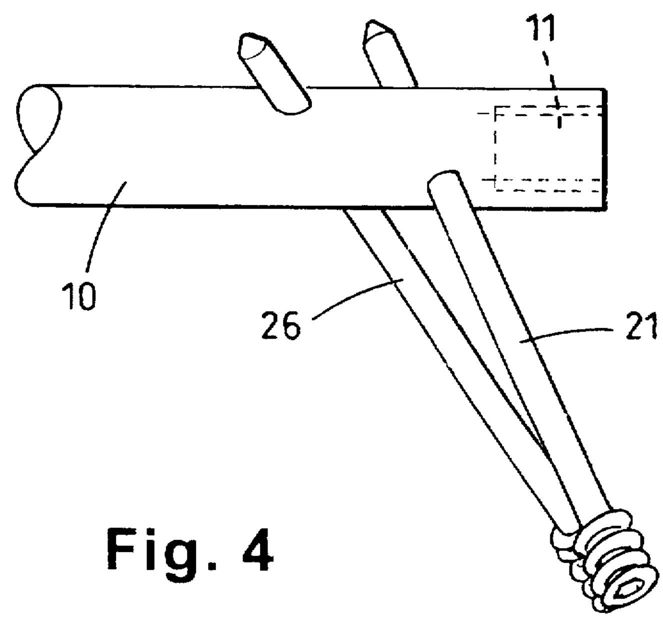
Figure 5:
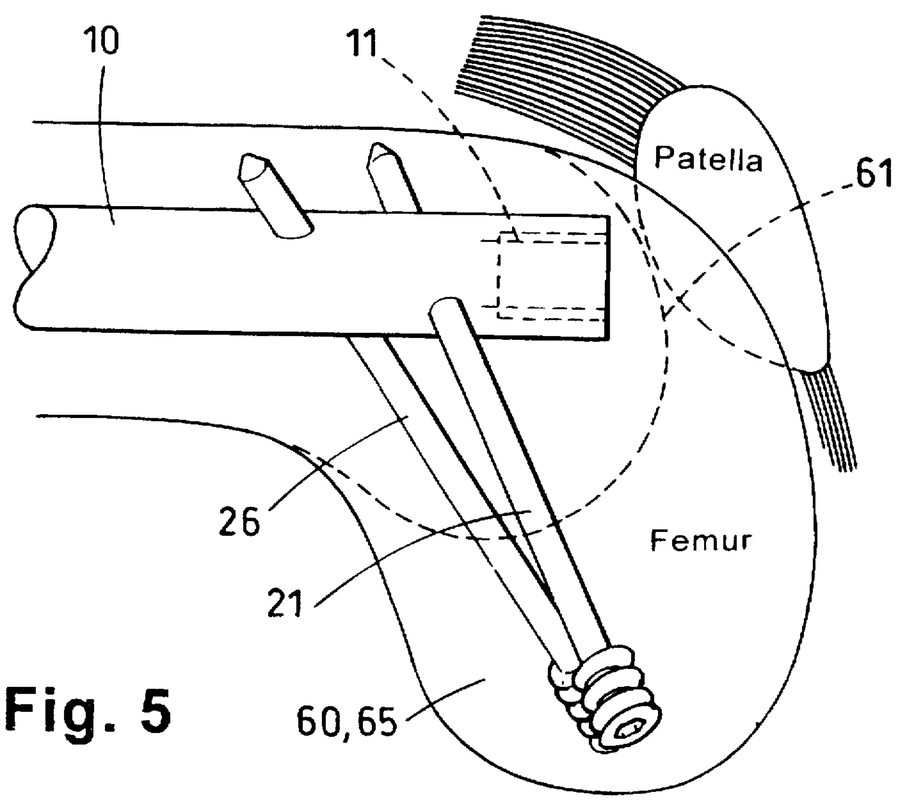
Figure 6:
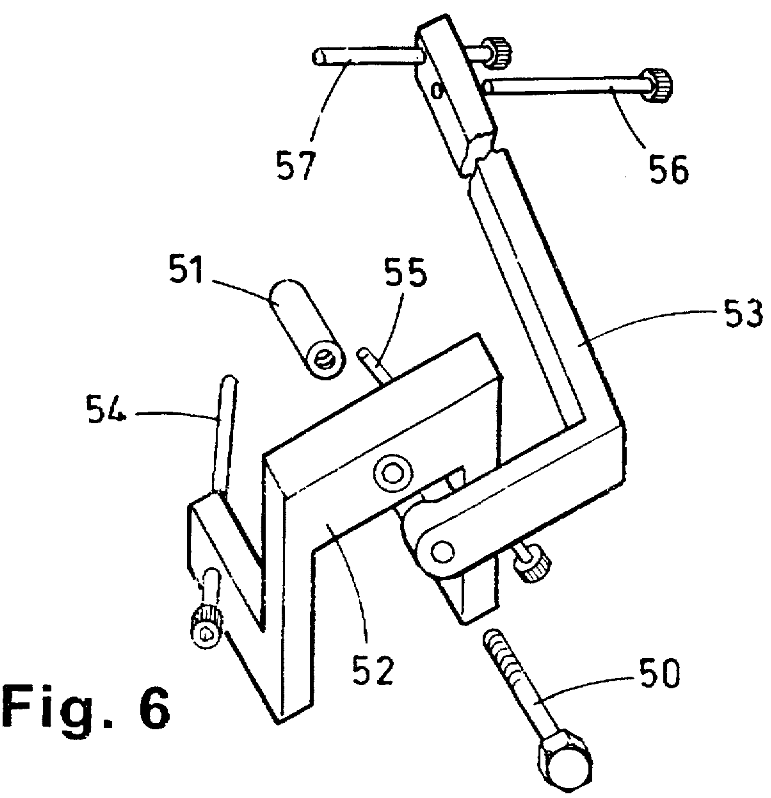
Figure 7A:
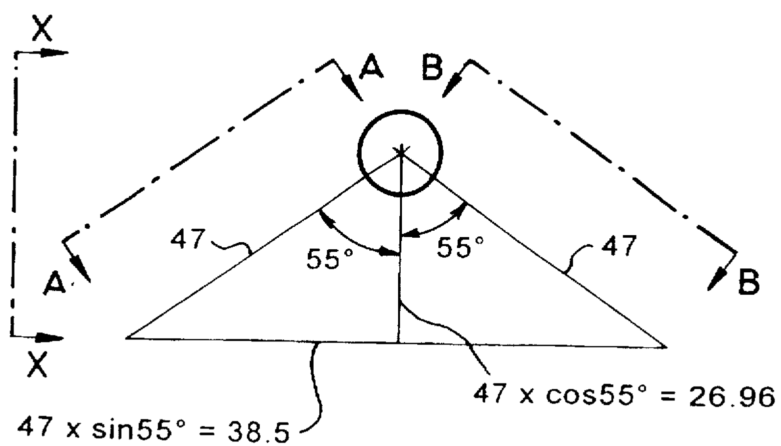
Figure 7B:
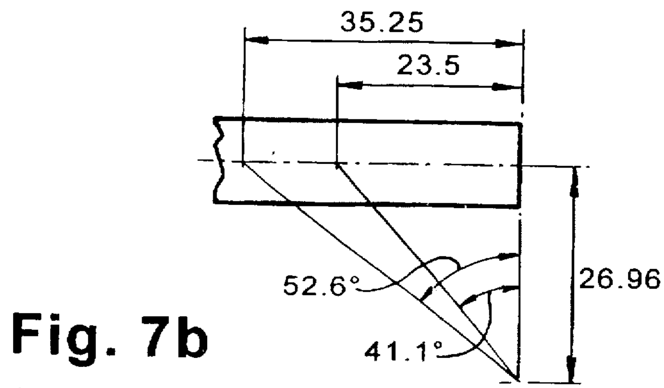
Figure 7C:
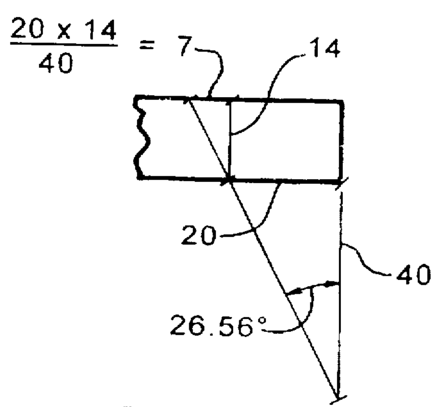
Figure 7D:
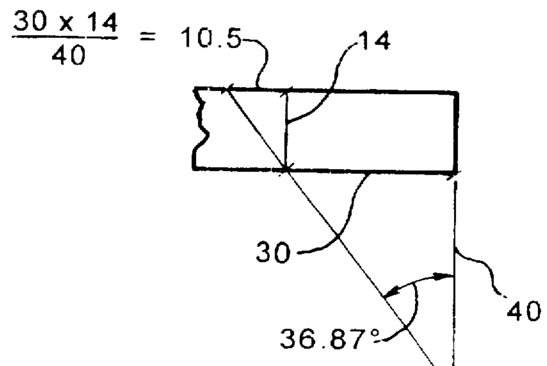
Figure 8:
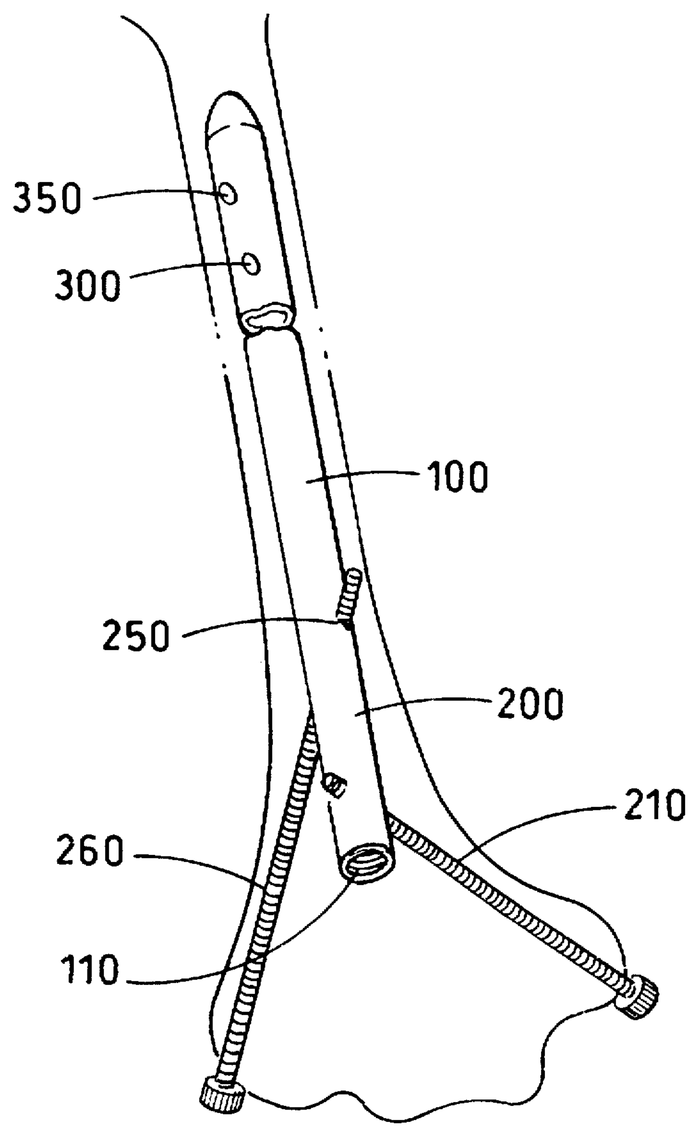

FIG. 1 is a perspective view of a nail according to the present invention showing its location in a femur;

FIG. 2 is a view similar to FIG. 1 except without the femur;

FIG. 3 is an axial view of a nail according to the present invention;

FIG. 4 is a lateral view of the nail according to the present invention;

FIG. 5 is a lateral view of the nail according to the present invention showing the femur;

FIG. 6 is a perspective view of a jig according to the present invention;

FIGS. 7(*a*) through 7(*d*) show approximate linear demensions and angular configurations of the distal locking bolts according to the present invention; and FIG. 8 is a perspective view of a nail according to the present invention showing its position in the distal end of the humerus.

FIG. 1 is a perspective view of the nail 10, showing its location in the distal end of a femur after insertion, and with locking bolts 21,26 in position passing through pre-drilled holes 20,25. Free holes 30,35 for insertion of proximal locking bolts are also shown.

FIG. 2 is a similar view of the nail shown in FIG. 1, but without the femur shown.

Alternative patterns of distal locking bolts are shown in FIGS. 1 and 2.

In FIG. 1, locking bolts are shown with smooth shanks 212, 262 which are an easy sliding fit in predrilled holes in the nail 20, 25. These locking bolts have coarse threads 211, 261 which grip the bone of the femoral condyles.

In FIG. 2, locking bolts of an alternative design are shown which have fully threaded shanks 214, 264. The threaded shanks are received in correspondingly threaded holes in the nail 10.

The head of all bolts 211, 261 and 213, 263 incorporate slots or sockets to accommodate an appropriate insertion wrench or screwdriver.

FIG. 3 is an axial view of the nail 10 and distal locking bolts 21,26 of FIG. 1 showing how the cross bolts are inserted to pass through the non-articular surfaces of the condyles (shown cross-hatched), while gripping the major mass of cancellous bone in each condyle 60,65.

FIGS. 4 and 5 show lateral views of the nail 10 and distal locking bolts 21,26.

FIG. 5 shows how the nail is to be positioned in the femur so that the distal end of the nail lies recessed below the articular surface of the intercondylar groove 61 of the femur so that it does not foul the trackin, of the patella. In this position, due to the obliquity of the cross bolts, these pass through the major mass of the cancellous bone of each condyle 60,65.

Intramedullary surgical nails in accordance with the invention are introduced into the femur through the knee. After surgically exposing the distal femur, an entry point is made in the intercondylar groove in line with the axis of the intramedullary canal. A guide wire or rod may be passed into the femoral intramedullary canal in order to assist the introduction of the nail into the canal. The nail may be of hollow section or "cannulated" so that it may be passed over the guide wire.

It is intended that insertion of the locking bolts will be facilitated by the use of a removable jig. This will be attached to the distal end of the nail which incorporates guide slots and a threaded axial hole 11, shown in FIGS. 1, 2, 4 and 5, for secure attachment to the jig, in the appropriate position to align the cross bolts with respect to the preformed holes in the nail. Typically, the attachment of the jig to the distal end of the nail will also be cannulated so that the jig may also pass over any guide wire used to introduce the nail into the femur.

FIG. 6 shows a perspective view of a typical jig for facilitating introduction of the nail and locking screws. The jig comprises parts 51, 52 and 53, securing bolt 50 and guide tubes 54, 55, 56 and 57.

The jig is employed as follows:

An extension piece 51 is attached to the distal end of the nail fitting rigidly to slots and threaded axial hole 11 in the nail 10. The distal locking guide 52 attaches rigidly to the extension piece 51. This may be achieved using a jig securing bolt 50 which mav be cannulated and engages in threads in extension piece 51. The distal locking guide 52 has predrilled guide holes through which guide tubes 54 and 55 may be passed. When the nail 10, extension piece 51 and distal locking guide 52 are rigidly coupled in this manner, the guide rubes 54,55 line up precisely with the predrilled distal holes in the nail 20,25. This permits drilling through the guide tubes to form holes through the femoral condyles in the correct position to pass through the existing predrilled distal holes 20,25 in the nail 10, and for subsequent insertion of the distal locking bolts 21 and 26.

The proximal locking guide arm 53 may be similarly attached to the extension piece 51. This incorporates predrilled guide holes through which guide tubes 56,57 may similarly be passed to align with the proximal predrilled holes 30,35 in the nail. Appropriately placed holes in the femoral shaft may be drilled and the proximal locking bolts inserted. The proximal locking guide arm 53 may be mounted either to the right as shown in FIG. 6 or to the left, so that the proximal cross bolts can be introduced from the lateral side for left and right femurs respectively.

Following insertion of the nail and all locking bolts, all components of the jig as above are disconnected and removed.

Typically, the nails may be manufactured in varying lengths and diameters from a biologically inert material which is sterilizable and has appropriate mechanical strength and stiffness, such as stainless steel. For the femoral nail, typical lengths are 250 to 360 mm. The section of the nail is typically tubular with an outer diameter of approximately 12 to 16 mm. The nail may be slightly bent to suit the curvature of the long bone. Distal cross bolts may be typically 6 to 11 mm outer diameter and approximately 75 to 85 mm long. Cross bolts may be partly or fully threaded.

Typical approximate linear dimensions (mm) and angular configuration (degrees) of the distal locking bolts in relation to a 14 mm diameter femoral nail are shown in FIGS. *7a–d.*

FIG. *7a* shows an axial view of a femoral nail similar to that shown in FIG. 3.

FIG. *7b* is a lateral view of the distal end of the femoral nail and distal locking bolts and in a similar projection to that shown in FIGS. 4 and 5.

FIGS. *7c* and *7d* are projections taken on the lines A—A and B—B, as shown in FIG. *7a*, showing distal locking bolts 21 and 26 respectively.

FIG. 8 is a perspective view of a humeral nail 100, showing its position in the distal end of the humerus with distal locking bolts 210,260 in position, passing through predrilled holes 200,250. Free holes 300,350 are provided for insertion of proximal locking bolts.

I claim:

1. A surgical intramedullary nail and locking bolt assembly for stabilizing fractures of the condyles and supracondylar region of the femur and humerus, said assembly comprising:

a nail in the form of a rod or tube having a longitudinal axis and adapted for insertion into an intramedullary canal through a distal end of a femur or humerus, said nail having first and second distal locking holes; and first and second distal locking bolts for insertion into the first and second distal locking holes;

the first and second distal locking holes being staggered and angled with respect to said longitudinal axis such that the distal locking bolts when inserted into said holes extend in a divergent manner from said nail and permit each condyle to be gripped by a respective one of the first and second locking bolts so as to stabilize the condyles with respect to the nail.

2. A nail as claimed in claim 1 wherein the distal locking bolts are positionable so as to pass through a non-articular portion of the condyles, while gripping the mass of cancellous bone in each condyle.

3. A nail as claimed in claim 1 designed for retrograde insertion into the femur or humerus from distal to proximal, and incorporating a means of attachment of a temporary jig to facilitate drilling of pilot holes and subsequent insertion of locking bolts.

4. A nail and locking bolt assembly as claimed in claim 1, wherein the distal locking holes are positioned at a distal end of the nail, wherein said distal end comprises a threaded axial hole.

5. A nail as claimed in claim 1, wherein said nail has one or more preformed proximal holes extending transversely through a proximal region of the nail to stabilize the nail with respect to the shaft of the femur or humerus.

6. A jig for facilitating the retrograde insertion of a surgical intramedullary nail into a femur or humerus from distal to proximal, said nail having a longitudinal axis, a proximal end and a distal end, the distal end having preformed holes which are staggered and angled with respect to the longitudinal axis such that distal locking bolts inserted into said holes extend in a divergent manner from said nail and permit each condyle to be gripped by a respective bolt, said jig comprising:

a frame having guide arms adapted to extend on either side of the knee or elbow, said frame including means for attachment to the distal end of the nail in a predetermined angular relationship therewith, and said guide arms having guide means for guiding the introduction of said locking bolts into said condyles and into said preformed holes.

7. A jig as claimed in claim 6, wherein said frame further comprises a reversible guide arm for the introduction of locking bolts from the lateral side for both right and left femora into preformed proximal holes in the nail.

8. A method of surgically stabilising a condylar or supracondylar fracture which comprises introducing an intramedullary nail into the femur or humerus through the intercondylar groove and inserting locking bolts through non-articular surfaces of the condyles and into holes in the nail.

9. A method as claimed in claim 8, wherein said locking bolts comprise shanks dimensioned at one end to fit into said holes in the nail and being formed at the other end with threads for engaging and gripping the condyles.

10. A method as claimed in claim 8, which includes the step of stabilizing said nail proximally by inserting proximal locking bolts into the femur or humerus and into proximal holes in said nail.

* * * * *